US012797545B2

(12) United States Patent
Atterbury et al.

(10) Patent No.: US 12,797,545 B2
(45) Date of Patent: Nov. 17, 2026

(54) AUTOINJECTOR AND METHOD OF INJECTING FLUIDS

(71) Applicant: Battelle Memorial Institute, Columbus, OH (US)

(72) Inventors: William G. Atterbury, Columbus, OH (US); Timothy M. Blum, Columbus, OH (US); David A. Holley, Lancaster, OH (US); John P. Tallarico, Powell, OH (US); Steven M. Madland, Columbus, OH (US)

(73) Assignee: Battelle Memorial Institute, Columbus, OH (US)

(*) Notice: Subject to any disclaimer, the term of this patent is extended or adjusted under 35 U.S.C. 154(b) by 0 days.

(21) Appl. No.: 18/473,857

(22) Filed: Sep. 25, 2023

(65) Prior Publication Data

US 2024/0091449 A1 Mar. 21, 2024

Related U.S. Application Data

(62) Division of application No. 16/845,065, filed on Apr. 9, 2020, now Pat. No. 11,801,346.

(Continued)

(51) Int. Cl.

| | |
|---|---|
| ***A61M 5/20*** | (2006.01) |
| ***A61M 5/315*** | (2006.01) |
| ***A61M 5/32*** | (2006.01) |

(52) U.S. Cl.

CPC ...... *A61M 5/2033* (2013.01); *A61M 5/31586* (2013.01); *A61M 5/3234* (2013.01);

(Continued)

(58) Field of Classification Search

CPC .. A61M 2005/2006; A61M 2005/2013; A61M 2005/202; A61M 2005/2026;

(Continued)

(56) References Cited

U.S. PATENT DOCUMENTS

| | | | |
|---|---|---|---|
| 7,381,201 B2 | 6/2008 | Gilbert et al. | |
| 7,887,506 B1 * | 2/2011 | Smolyarov ............. | A61M 5/30 604/68 |

(Continued)

OTHER PUBLICATIONS

International Preliminary Examination Report on Patentability from International Application No. PCT/US2020/027561 issued Nov. 2, 2021.

(Continued)

*Primary Examiner* — Michael J Tsai
*Assistant Examiner* — Neeraja Gollamudi
(74) *Attorney, Agent, or Firm* — Susanne A. Wilson; Frank Rosenberg

(57) ABSTRACT

An autoinjector and method of injection are described. A power spring causes rotation of a drive nut about the central axis of the autoinjector that, in turn, causes a middle screw to rotate in the same direction as the drive nut and also to move in the distal direction while pushing a center screw in the distal direction that pushes the syringe and needle. The center screw also pushes a plunger that pushes the fluid out of the syringe. After injection, a locked retract screw is freed and rotates in the same direction as the middle screw causing the syringe to retract the syringe into the housing.

20 Claims, 13 Drawing Sheets

Related U.S. Application Data

(60) Provisional application No. 62/844,055, filed on May 6, 2019.

(52) U.S. Cl.
CPC ............... *A61M 2005/2013* (2013.01); *A61M 2005/202* (2013.01); *A61M 2005/206* (2013.01); *A61M 2005/2073* (2013.01); *A61M 2005/208* (2013.01); *A61M 2005/2086* (2013.01)

(58) Field of Classification Search
CPC ............ A61M 5/2033; A61M 5/31586; A61M 5/3234; A61M 2005/206; A61M 2005/2073; A61M 2005/208; A61M 2005/2086
See application file for complete search history.

(56) References Cited

U.S. PATENT DOCUMENTS

| | | | | | |
|---|---|---|---|---|---|
| 8,734,394 | B2 * | 5/2014 | Adams | A61M 5/326 | 604/242 |
| 8,808,250 | B2 | 8/2014 | Ekman et al. | | |
| 9,242,044 | B2 | 1/2016 | Markussen | | |
| 10,201,658 | B2 | 2/2019 | Kemp et al. | | |
| 10,232,116 | B2 | 3/2019 | Ekman et al. | | |
| 11,684,724 | B2 | 6/2023 | Egesborg et al. | | |
| 2002/0095120 | A1 | 7/2002 | Larsen et al. | | |
| 2013/0123697 | A1 * | 5/2013 | Ekman | A61M 5/326 | 604/110 |
| 2013/0131602 | A1 * | 5/2013 | Kemp | A61M 5/3202 | 604/197 |
| 2013/0267908 | A1 * | 10/2013 | Leak | A61M 5/31545 | 604/191 |
| 2016/0022911 | A1 * | 1/2016 | Tsui | A61P 23/00 | 604/58 |
| 2018/0200442 | A1 * | 7/2018 | Atterbury | A61M 5/3287 | |

OTHER PUBLICATIONS

Written Opinion of the International Search Authority from International Application No. PCT/US2020/027561 mailed Jul. 29, 2020.
International Search Report from International Application No. PCT/US2020/027561 mailed Jul. 29, 2020.
Extended European Search Report and Search Opinion in European Patent Application No. EP24221695.0A issued Apr. 15, 2025.

* cited by examiner

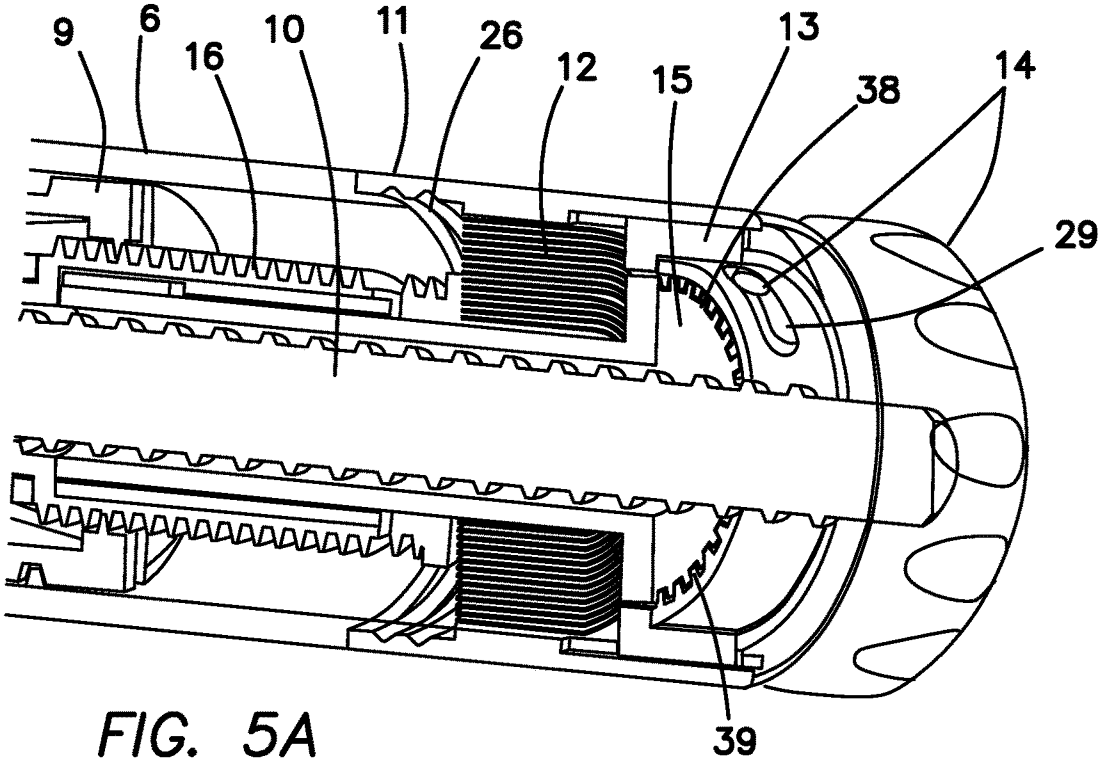
FIG. 5A
FIG. 5B
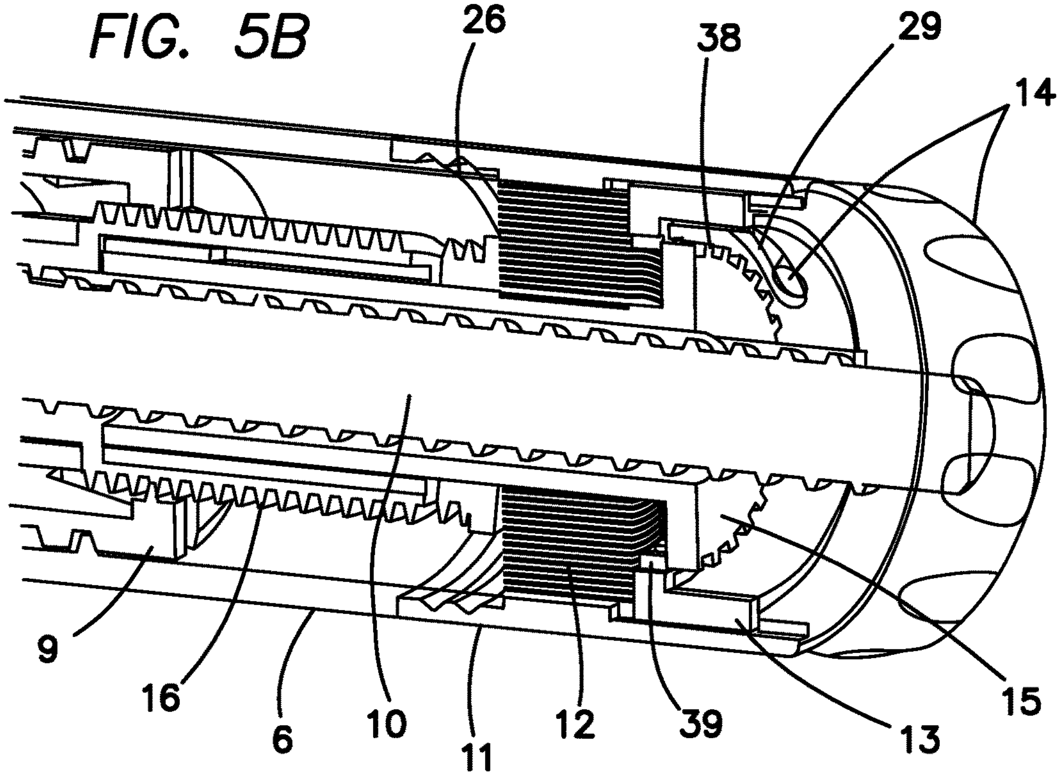

AUTOINJECTOR AND METHOD OF INJECTING FLUIDS

RELATED APPLICATIONS

This application is a division of U.S. patent application Ser. No. 16/845,065, filed on Apr. 9, 2020 which claims the priority benefit of U.S. Provisional Patent Applications No. 62/844,055 filed May 6, 2019.

INTRODUCTION

Injecting a medication involves the steps of insertion of the needle into the patient, injection of the appropriate dose of medicine, and retraction of the needle out of the patient into a position in which the needle is withdrawn. Over the years, extensive efforts have been expended in developing improved injection methods and spring-powered autoinjectors.

Ekman et al. in U.S. Published Patent Application No. 20130123697 describes an autoinjector with a torsion spring that is used for inserting the needle, emptying the syringe and then retracting the needle and syringe. The autoinjector is activated by pressing a trigger button that releases the torsion spring to exert a force on a stopper and syringe. Eckman et al. report that the lead screw thread has a variable pitch arranged to advance a second gear member faster and with less force when inserting the needle (steep pitch) and more slowly with increased force while expelling the medicament in the syringe.

Kemp et al. in U.S. Pat. No. 10,201,658 describes an autoinjector that is activated by a button and inserts a needle, injects a medication, and retracts the needle after injection. In this autoinjector, power is supplied by a torsion spring that lengthens as it unwinds. In this device, a lead screw is fixed rotationally and moves axially, and a retraction slider tube that is fixed both rotationally and axially during the initial phase. In order to prevent the drive mechanism from locking up, the drive mechanism must increase delivered force in order to collapse a viscous damper; should this occur too early, the device would fail to deliver the complete dose of medicine.

Other autoinjector devices capable of injection and retraction are described by Ekman et al. in U.S. Pat. No. 10,232,116, Larsen et al. in US 2002/0095120, and Markussen et al. in U.S. Pat. No. 9,242,044.

Despite these and other efforts, there remains a need to develop injection methods and autoinjectors with improved characteristics such as relatively simpler and more compact design, softer needle insertion, and the ability to reliably deliver viscous drugs and high volume doses.

SUMMARY OF THE INVENTION

In a first aspect, the invention provides a method of advancing and retracting a needle in a cylindrical autoinjector having an axis between a distal end and a proximal end of the autoinjector, comprising: providing an autoinjector, comprising a power spring, a drive nut, a middle screw, a center screw, a syringe with needle, a fluid in the syringe, and a retract screw, all contained within a housing; freeing a drive nut from a locked position within a housing of an autoinjector, wherein the drive nut is connected distally to a power spring; wherein the power spring causes rotation of the drive nut about the central axis of the autoinjector; wherein the rotation of the drive nut causes the middle screw to rotate in the same direction as the drive nut and also to move in the distal direction while pushing the center screw in the distal direction; wherein the center screw pushes the syringe and needle in the distal direction; wherein, subsequent to the syringe and needle being fully extended, the center screw pushes a plunger that pushes the fluid out of the syringe; wherein, subsequent to the plunger bottoming out in the syringe, a locked retract screw is freed and rotates in the same direction as the middle screw; and wherein rotation of the retract screw causes the retract screw to move in the proximal direction; wherein the retract screw is connected to the syringe so that movement of the retract screw in the proximal direction causes the syringe to move in the proximal direction and retract the syringe into the housing.

In some embodiments, the invention includes one or any combination of the following features: wherein the middle screw is part of a double-acting screw that comprises a center screw that is fixed to prevent rotation and that moves in the distal direction at a rate faster than the middle screw; wherein the center screw is prevented from rotating during needle insertion and fluid delivery by being keyed to a syringe carrier that is keyed to a flange capture nut that is keyed to the housing or is keyed to a tab disk that is keyed to a retract screw; wherein the autoinjector includes a delay nut that continues to drive the center screw in the distal direction after the center screw disengages from the middle screw; wherein the rotation of the delay nut drives the center screw distally so that the center screw pushes the plunger until the plunger bottoms out in the syringe; wherein the bottoming of the plunger in the syringe activates the delay mechanism that provides a short time delay between the bottoming of the plunger and the retract mechanism; wherein the delay mechanism begins when plunger bottoms the syringe, which causes the center screw to stop advancing, which causes the delay nut to stop rotating and the middle screw to continue rotating at a slower rate due to the damping grease between the middle screw and the delay nut; wherein the external threads of the middle screw have a smaller pitch than the threads of the center screw, causing the center screw to advance in the distal direction at a faster rate than the middle screw; wherein the differing pitch of the external threads of the middle screw to the threads of the center screw varies the force applied to the plunger during delivery; wherein the differing pitch of the external threads of the middle screw to the threads of the center screw varies the force applied to the plunger in response to differing loads to the mechanism; wherein the double acting screw comprises a middle screw and a center screw that have threads in the same direction with varying pitch to effect force multiplication or reduction; wherein the double acting screw comprises a middle screw and a center screw that have threads in the opposite direction with varying pitch to effect force multiplication or reduction; wherein the external threads of the middle screw and the threads of the center screw may vary in pitch along their respective lengths to vary the force applied during a stroke; and/or wherein the step of freeing comprises a step of pressing a distal end of the autoinjector against the body of a human or non-human animal.

In a second aspect, the invention provides an autoinjector having a central axis within a housing, comprising: a power spring disposed at a proximal end of the autoinjector; a drive nut connected at the distal end to the power spring; a middle screw cylindrically disposed about the drive nut; wherein the middle screw is an outer part of a double-acting screw and a center screw is an inner part of the double-acting screw; wherein threads of an inner diameter of the middle screw and outer diameter of the center screw interact so that rotation of the middle screw, when driven by the drive nut, causes the center screw to advance in the distal direction; a syringe disposed along the central axis and comprising a plunger and a tip or needle hub disposed distally of the center screw so that movement of the center screw pushes the plunger; a retract screw cylindrically disposed about the middle screw and having threads on the outer circumference that match with threads on the inner circumference of the housing such that rotation of the middle screw moves the retract screw in the proximal direction. The autoinjector has the functionality (is capable of) the method described above.

In some embodiments, the invention includes one or any combination of the following features: further comprising a delay nut disposed on the distal end of the middle screw and having damping grease disposed between the middle screw and the delay screw; further comprising a power spring that is bi-metallic that causes changes in torsion that are temperature-dependent; further comprising a middle screw whose outer diameter threads have a smaller pitch than the threads of a center screw, causing the center screw to advance in the distal direction at a faster rate than the middle screw; further comprising a middle screw and a center screw that have threads in the same direction with varying pitch, providing the capability of effecting force multiplication or reduction; further comprising a middle screw and a center screw that have threads in the opposite direction with varying pitch, providing the capability of effecting force multiplication or reduction; further comprising a double-acting screw wherein the external threads of the middle screw and the threads of the center screw may vary in pitch along their respective lengths to vary the force applied during a stroke; further comprising a flange capture nut that connects the syringe axially via a syringe carrier to the retract screw, allowing the syringe to retract with the retract screw.

In a further aspect, the invention provides an autoinjector comprising a temperature-compensated power spring comprising a torsion spring that is bi-metallic so that the torque provided by the power spring remains consistent over a range of temperatures. Additionally, in some preferred embodiments, the methods or apparatus described herein could include a temperature-compensated power spring.

BRIEF DESCRIPTION OF THE DRAWINGS

FIGS. 5A-5B are schematics cross-sectional views illustrating the release of the drive nut from stored position.

GLOSSARY

Figure 1:
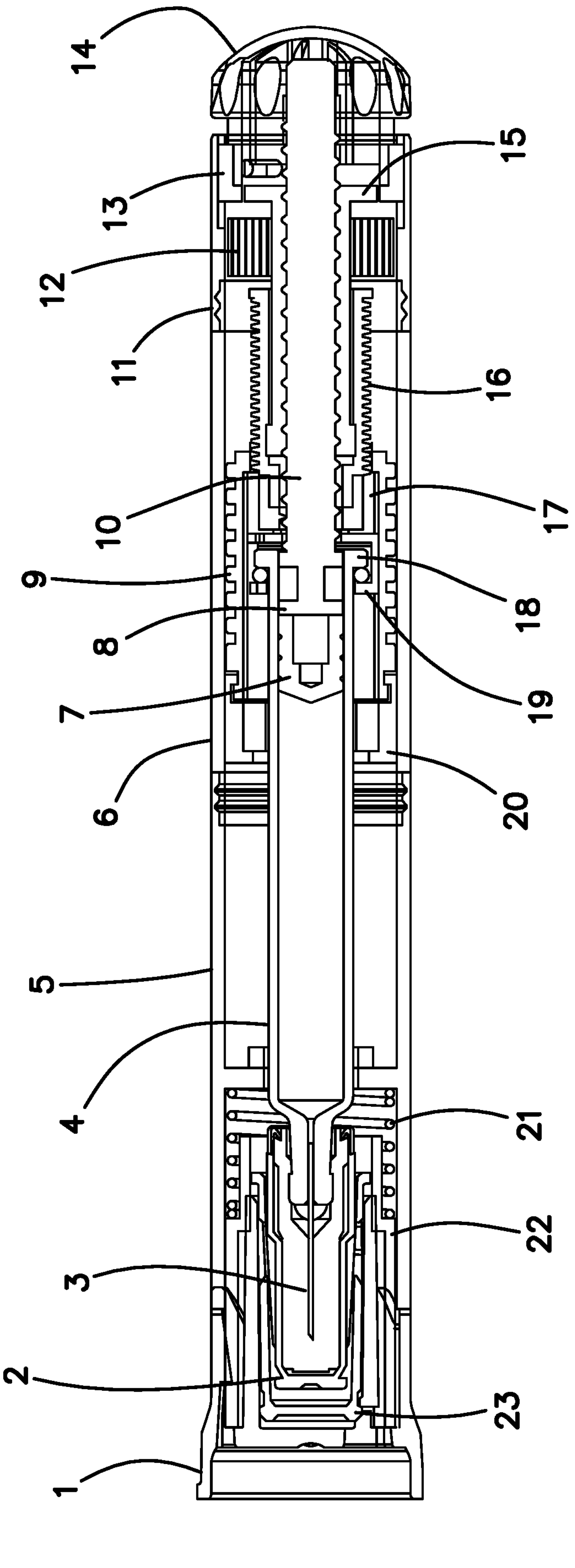
FIG. 1 is a schematic cross-sectional view of the autoinjector.
Figure 2A:
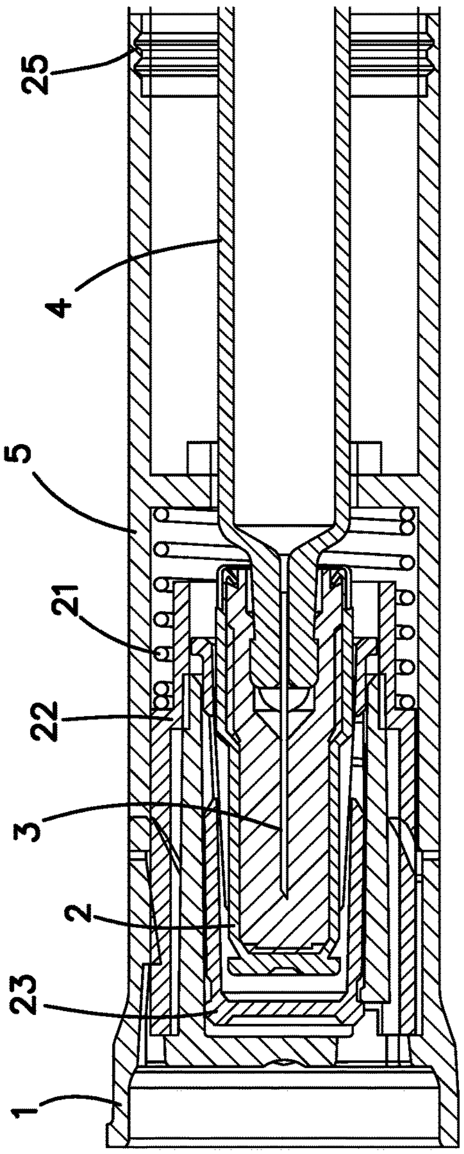
FIGS. 2A-2B show magnified cross-sectional views of the autoinjector.
Figure 2B:
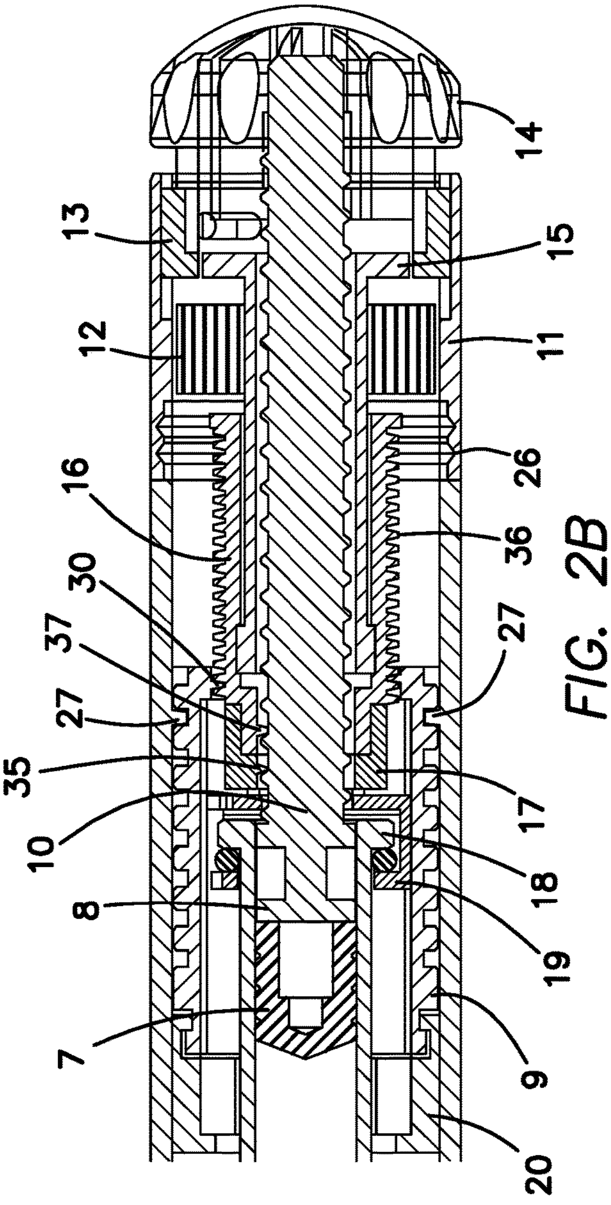
Figure 3A:
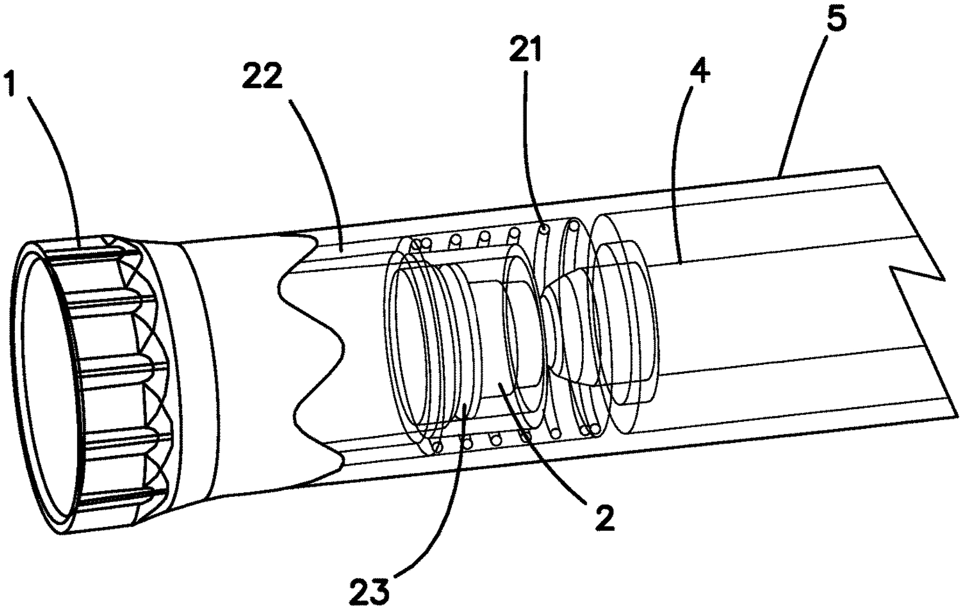
FIGS. 3A-3B are schematics illustrating removal of the basecap.
Figure 3B:
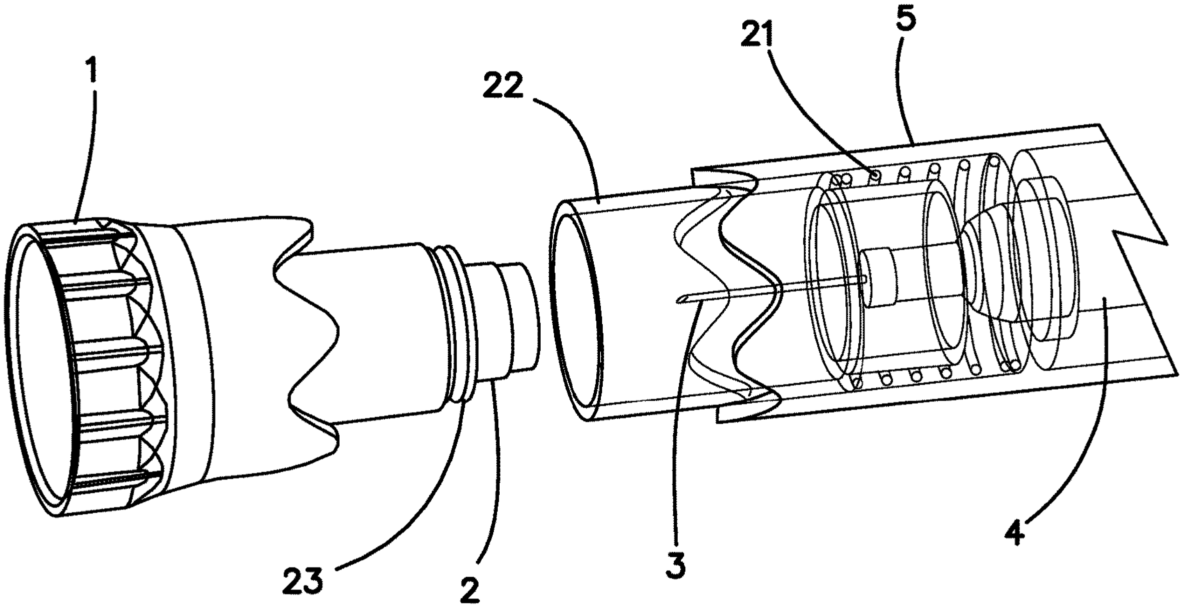
Figure 4A:
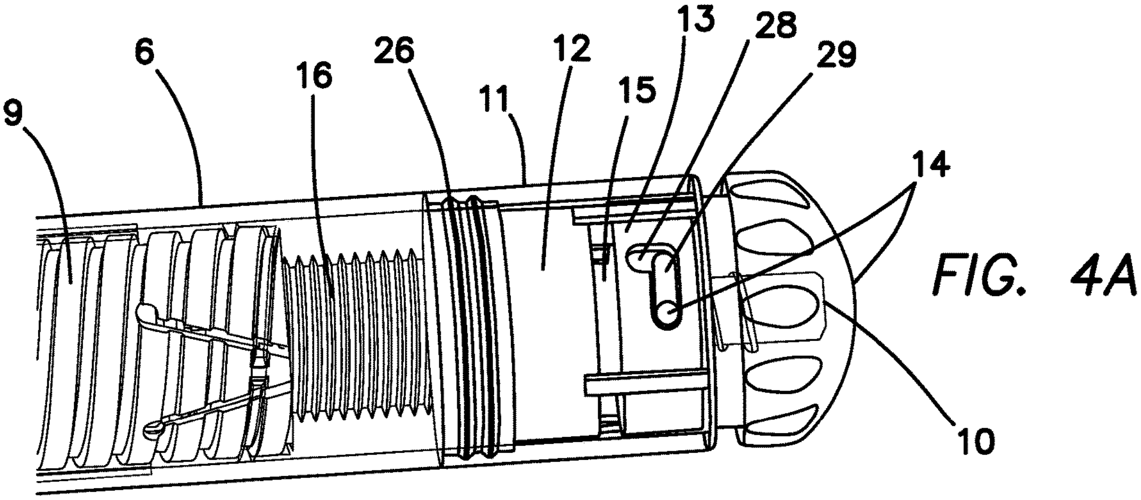
FIGS. 4A-4C are schematics illustrating the button in stored, unlock, and activate positions.
Figure 4B:
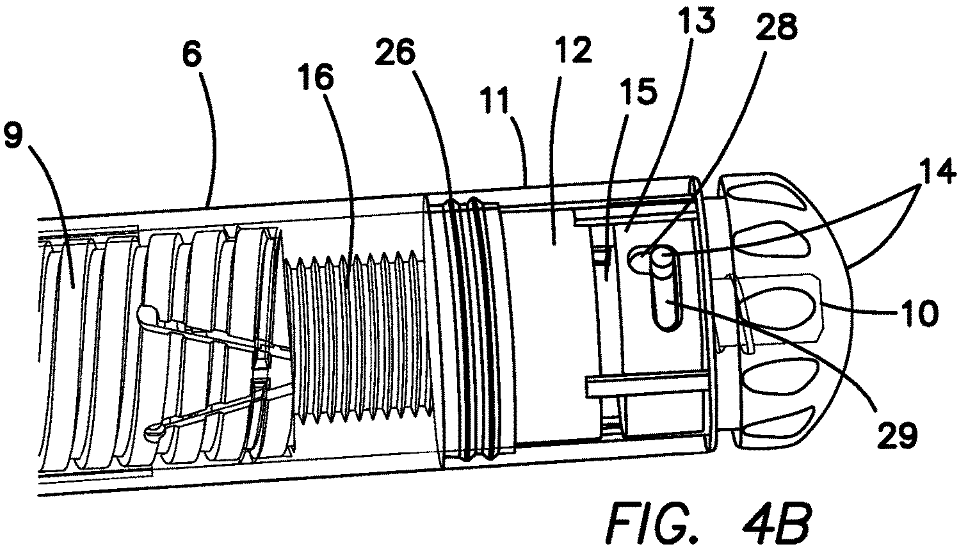
Figure 4C:
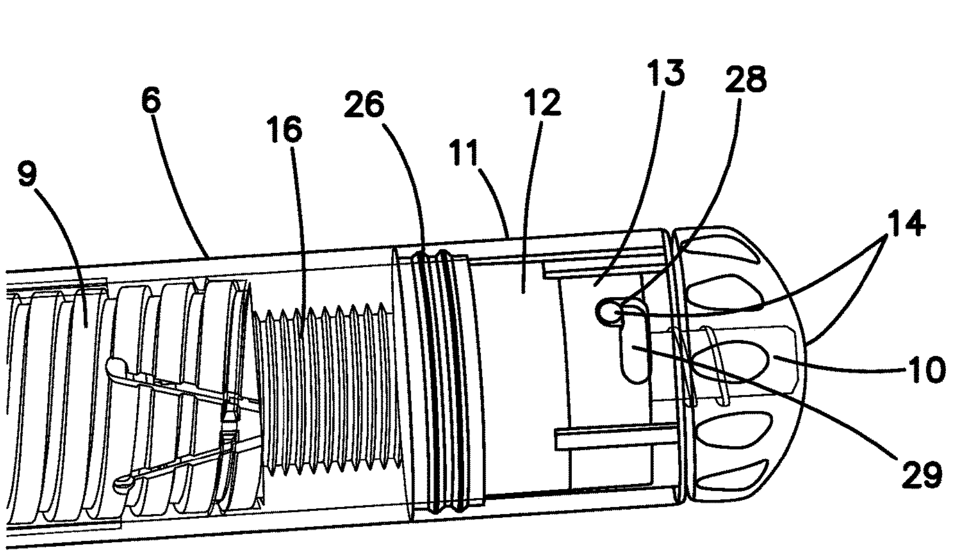
Figure 6:
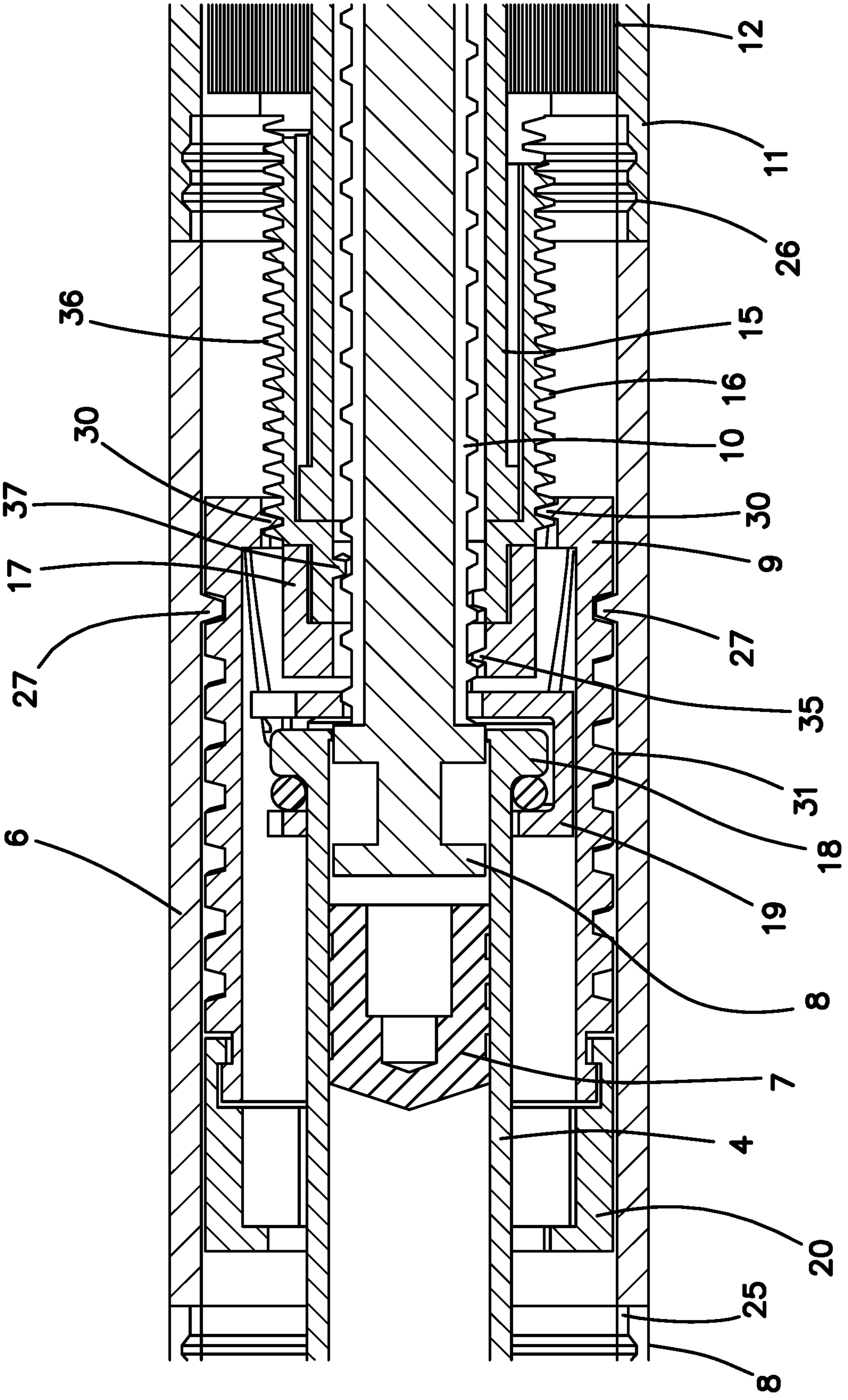
FIG. 6 is a close up schematic cross-sectional view illustrating the rotational mechanism in stored condition.
Figure 7:
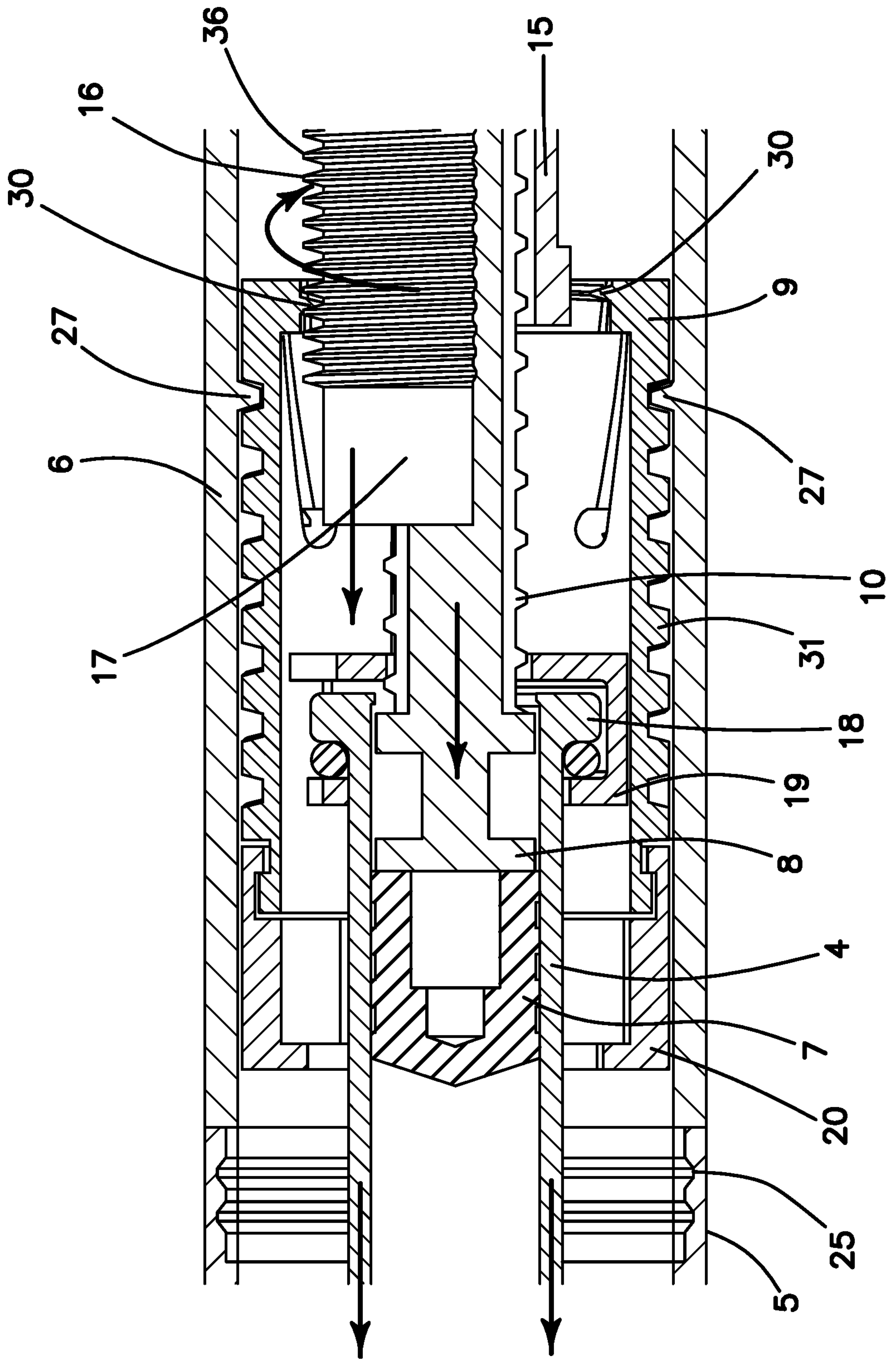
FIG. 7 is a close up schematic cross-sectional view of the rotational mechanism part way through the needle insertion phase.
Figure 8:
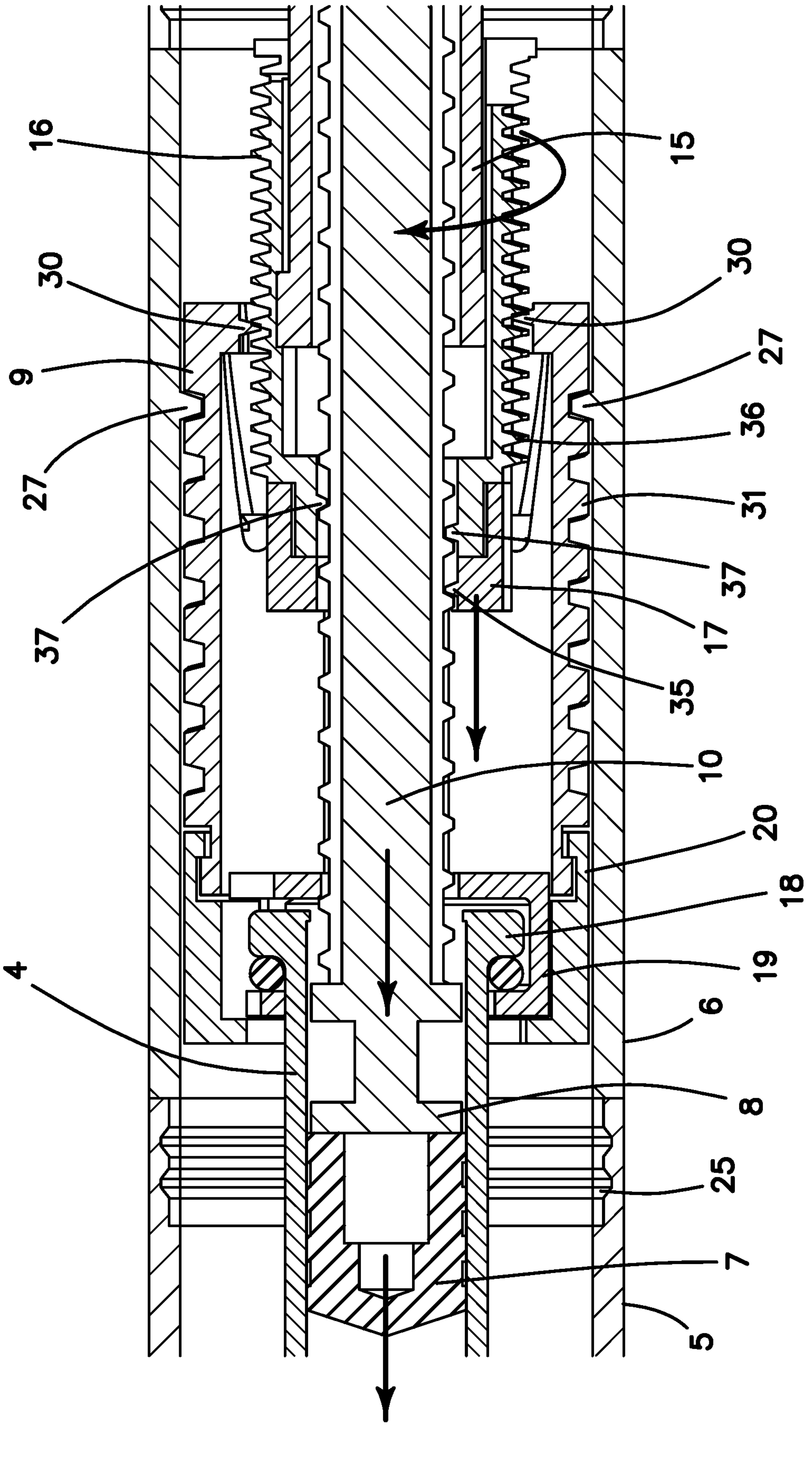
FIG. 8 is a close up schematic cross-sectional view of the rotational mechanism part way through the fluid injection phase.
Figure 9:
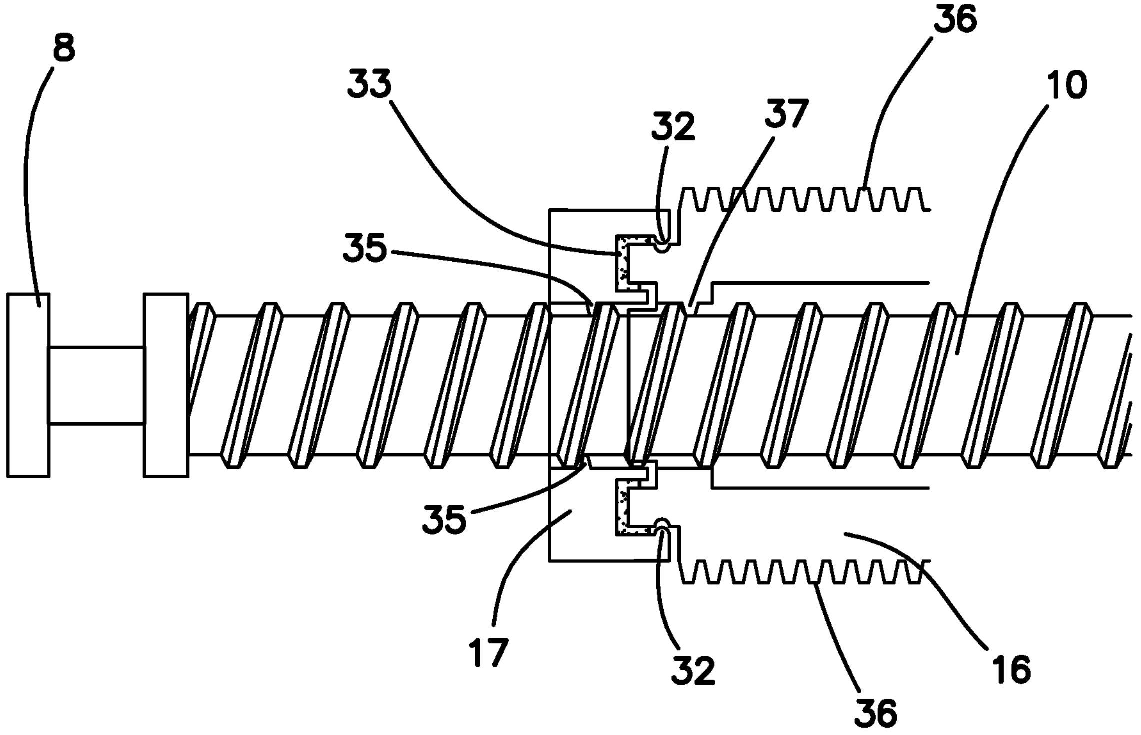
FIG. 9 is a schematic cross-sectional view of the delay mechanism.
Figure 10:
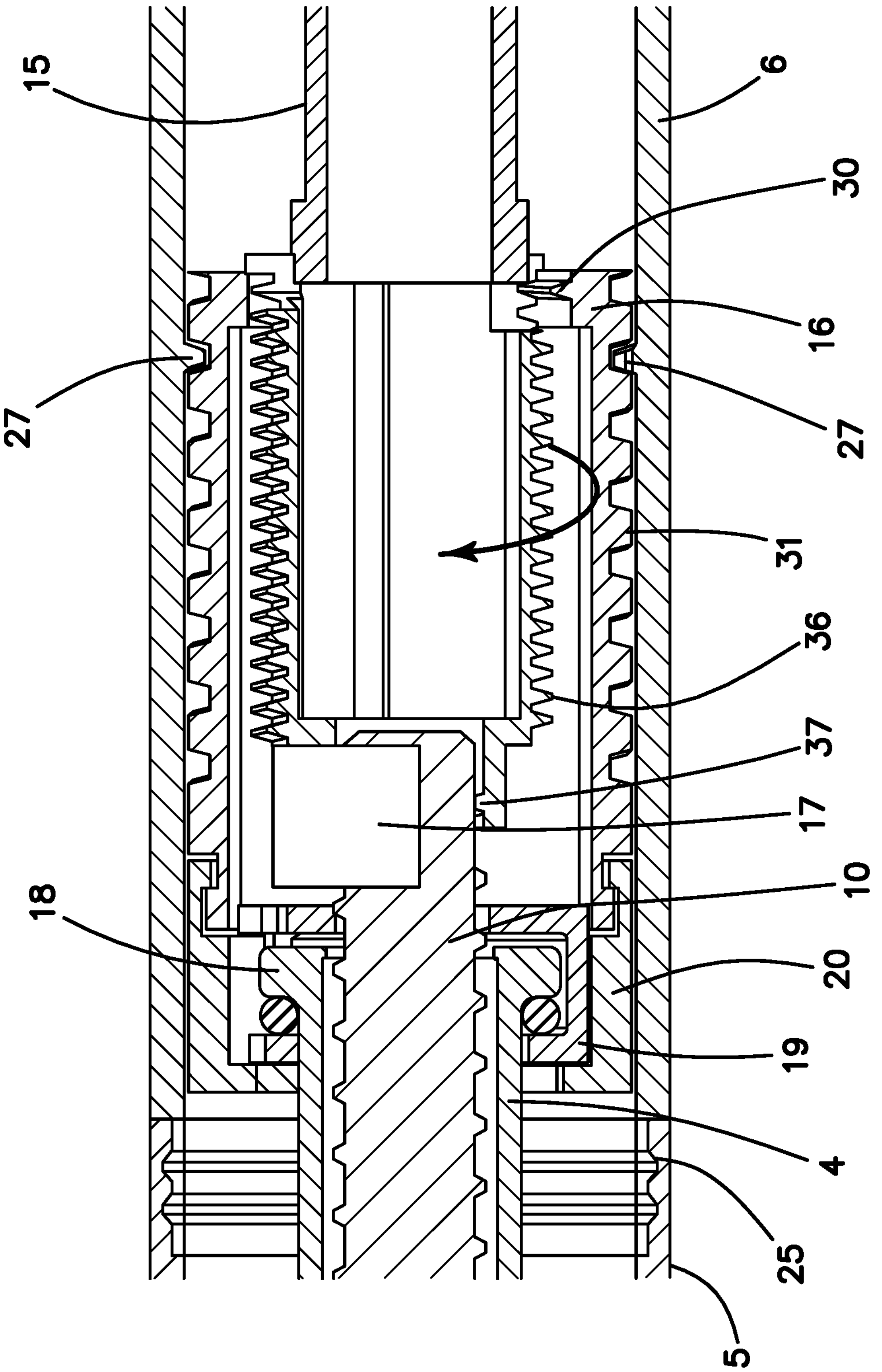
FIG. 10 is a close up schematic cross-sectional view of the rotational mechanism at initiation of the delay mechanism.
Figure 11A:
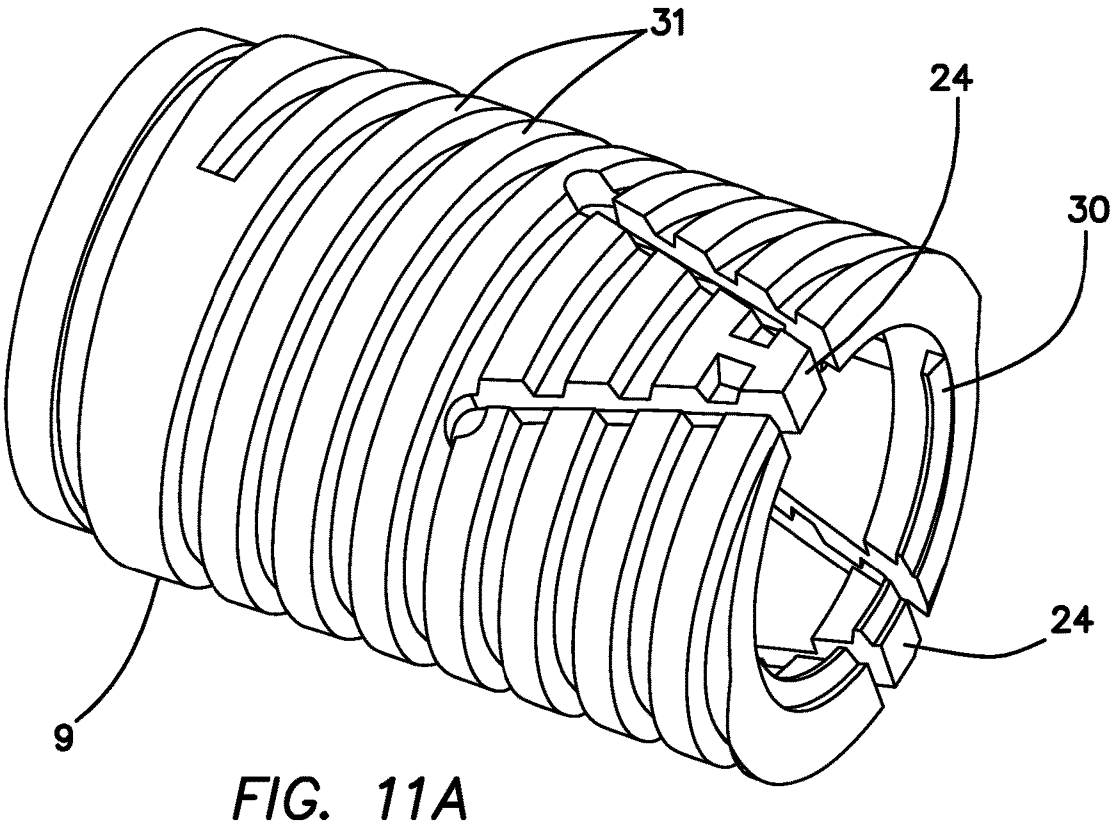
FIGS. 11A-11B are close up schematics of the retract screw and the middle screw.
Figure 11B:
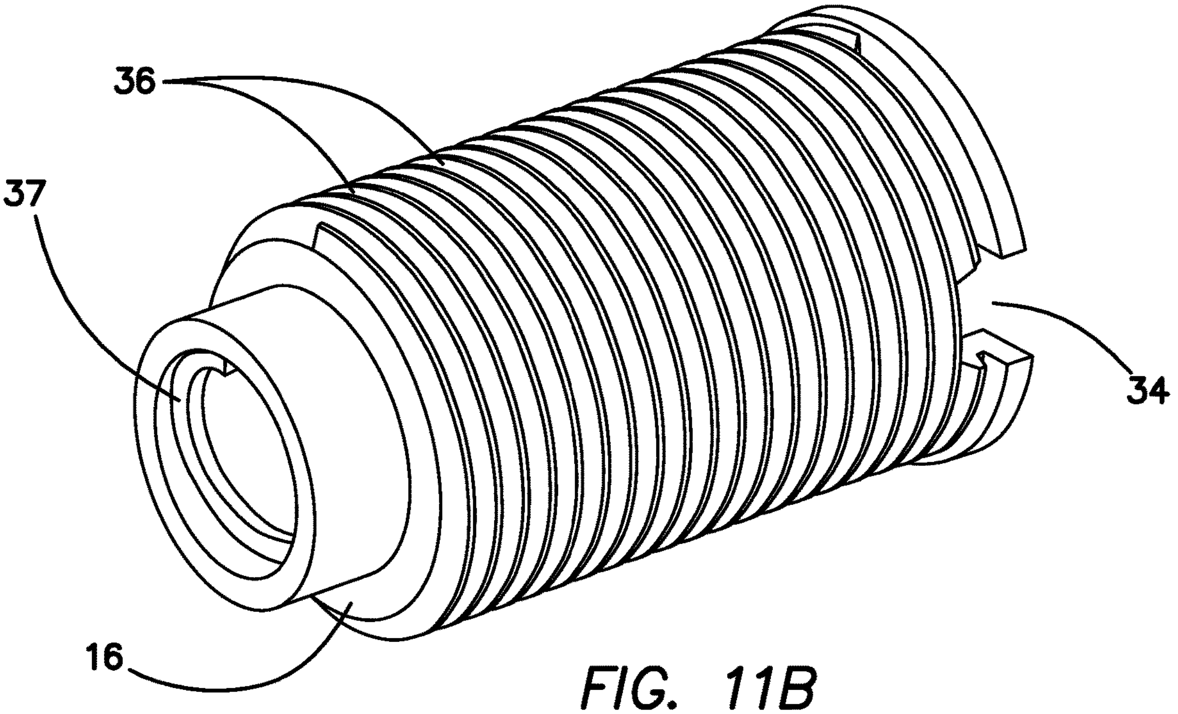
Figure 12:
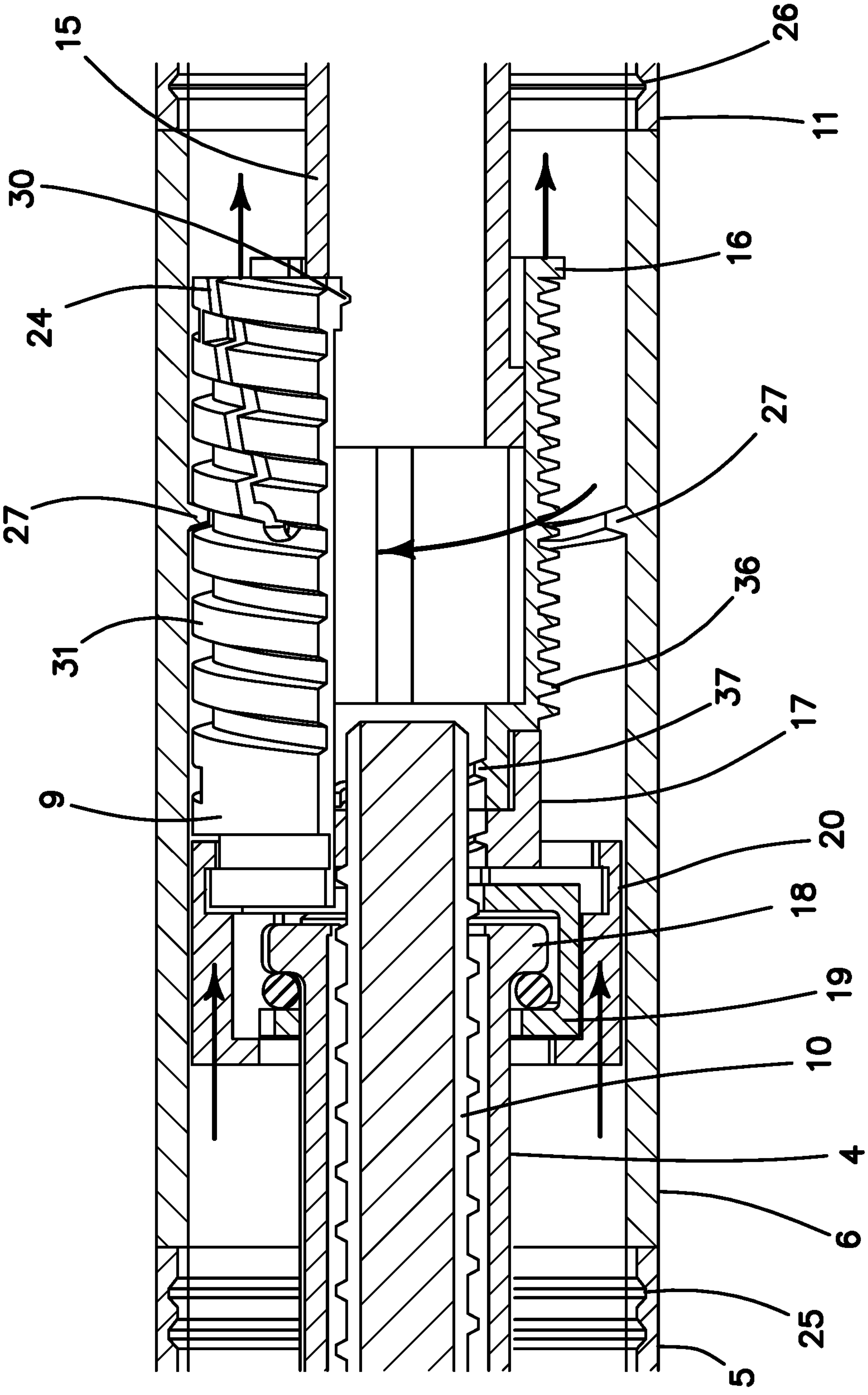
FIG. 12 is a close up schematic cross-sectional view of the rotational mechanism part way through the retraction phase.
Figure 13:
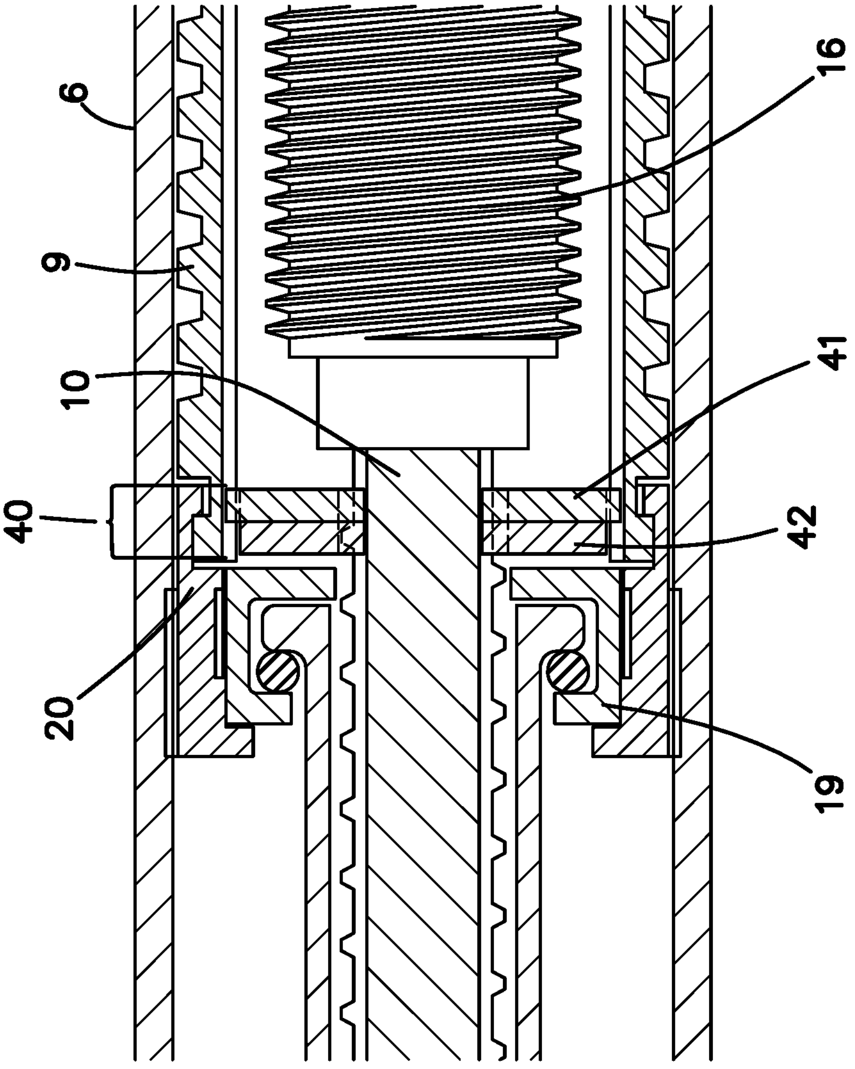
FIG. 13 is a close up schematic of an alternative retraction mechanism.

The proximal end is the end directed away from the patient.

The distal end is the end directed towards the patient.

A stroke encompasses the events between activating the device and completed injection of the fluid medication.

The driving force is the axial force directed along the vector from the proximal end to the distal end that expels the fluid medicine from the syringe (typically a cylindrical syringe); and, typically, also pushes the needle through the skin of the patient.

A torsion spring is an elastic object that stores mechanical energy when it is twisted. In this invention, a preferred form of a drive spring is a torsion spring. In this invention, the most preferred form of drive spring is also known as a clock spring.

Various aspects of the invention are described using the term "comprising;" however, in narrower embodiments, the invention may alternatively be described using the terms "consisting essentially of" or, more narrowly, "consisting of."

Description of Some Preferred Embodiments of the Autoinjector

The assembled autoinjector that is ready for use begins with: a syringe with a needle at the distal end; a middle screw and center screw in a stored state; a drive nut positioned between the middle screw and center screw; a retract screw disposed around the middle screw; and a housing around the retract screw and extending over the syringe and needle. The drive nut is connected to a pre-loaded power spring (which is preferably a watch spring that does not extend in the axial direction during release) and locked to the housing. As shown in the figures, the components are generally cylindrical and nested within each other to achieve a highly compact device.

The device is activated by the operator (typically the person to be injected) by pushing a button or switch (not shown) or housing against the skin that releases the drive nut from its lock with the housing. Prior to use, the syringe is loaded with a fluid medicine. Typically, the medicine is separated from the head of a plunger by a seal. In some embodiments, the seal and plunger head can be combined, and/or the center screw and plunger can be combined; alternatively, the center screw comprises a foot that presses against the plunger when the center screw is advanced. In the drawing, the foot is shown separate from the plunger; however, these two elements could be reduced to a single element. Friction between the plunger and the syringe wall prevents ejection of medication while the syringe is advanced so that the needle enters the patient. The end of the syringe moves until it abuts the patient's skin (there could be a mechanical insertion stop in the device) and then the friction is overcome and the movement of the plunger pushes medication through the needle.

The middle screw is part of a double-acting screw with threads on the outer surface that contacts the retract screw and threads on the inner surface that contacts a center screw, which is the other part of the double-acting screw, that telescopes out of the middle screw and pushes a foot in the distal direction. The middle screw is rotatable while the center screw is fixed to prevent rotation. The double-acting screw is configured so that when the drive nut rotates, the middle screw and center screw move in the distal direction in concert, but at different rates. The center screw is configured to advance the syringe and plunger. The threads of the center screw and the external threads of the middle screw have threads in the opposite direction. The threads of the center screw have a larger pitch than the outside threads of the middle screw so that the center screw travels two times (or adjustable to any desired ratio) as fast as the middle screw.

Disposed on the distal end of the middle screw is a rotatable delay nut that is separated from the middle screw by a layer of damping grease. A rotational detent maintains a connection between the middle screw and delay nut. To ensure an accurate and complete dose, a delay nut continues to turn and drive the center screw in the distal direction until the plunger bottoms out. A detent provides a means for alignment until sufficient load is applied. In preferred embodiments, the damping nut continues to apply force on the center screw for 0.5 to 3 seconds, more preferably 1 to 2 sec. The middle screw never locks, it must keep turning to release the retract screw to allow the retract mechanism to function properly.

A retract screw is circumferentially disposed around the middle screw. The retract screw is locked in place until the end of stroke. Movement of the middle screw can release the retract screw, allowing the retract screw to retract in the proximal direction. A flange on the retract screw is interlocked with a flange on the flange capture nut. Since the flange capture nut is connected to the syringe, proximal movement of the retract screw retracts the flange capture nut and the syringe. The retract screw and flange capture nut are moveable over a distance that is sufficient to retract the needle into the housing; for example, moveable over a distance of 1 to 3 cm, or 1 to 2 cm. A gap between the retract screw and a flange capture nut, as shown in the drawings, can be used to cover tolerances so that the mechanism can begin retracting after the delay nut is released and before the middle screw bottoms out.

In storage, the housing extends over all the components and is at least partially threaded on the interior to interact with the retract screw. With this configuration, the operations of needle insertion; fluid medicine injection; and needle retraction can be accomplished with just one spring.

The invention includes any combination or subcombination of the components described or illustrated in this application. The autoinjector is suitable for both subcutaneous and intramuscular injections and any type of injectable medicine including biologics, insulin, and small molecule medicines such as epinephrine, atropine, and naloxone.

Components of the Autoinjector

In a preferred embodiment as illustrated in the figures, the autoinjector comprises:

A power spring 12 that is a torsion spring, preferably a clock spring, with tabs on the inner and outer ends. The tab on the outer end secures the spring to the housing. The tab on the inner end secures the power spring 12 to the drive nut 15. The power spring 12 may be bi-metallic so that wind (torque) changes with temperature. This will help compensate for fluid viscosity changes and give more torque at lower temperatures. This will also keep injection times more consistent with variation in temperature.

A drive nut 15 with keys that drive the middle screw 16 and splines 38 that key to the lock ring 13. The coupling between the drive nut 15 and the lock ring 13 retains the power spring 12 in stored condition.

A middle screw 16 with outer diameter right-handed threads 36 that engage the retract screw 9 and inner diameter left-handed threads 37 that engage the center screw 10. The external thread 36 pitch of the middle screw 16 may vary along its length, which causes to the force applied to the plunger 7 through the center screw 10 to vary. The middle screw 16 is rotated by the drive nut 15 and has cutouts 34 on its proximal end to release the retract screw latches 24 at the end of stroke.

A center screw 10 with left-handed threads that engage the internal threads of the middle screw 37. The center screw 10 keys to the syringe carrier 19, which keys to the flange capture nut 20 and the retract screw 9, preventing the center screw 10 from spinning during insertion and injection. The center screw 10 pushes on the plunger 7 in the distal direction. The center screw 10 threads may have a different pitch from the internal threads 37 of the middle screw 16 and may have pitch that varies along its length.

A retract screw 9 with left-handed threads on its outer diameter 31, which engage the middle housing 6, and right-handed threads on its inner diameter 30, which engage the middle screw 16. The retract screw 9 has latches 24 that release the retract screw 9 at the end of the stroke, with a groove that provides an active connection to the flange capture nut 20, allowing free rotation.

A syringe 4, typically cylindrical, that contains a plunger 7 and holds a needle 3.

A syringe needle 3 that is attached to the distal end of the syringe 4.

A flange capture nut 20 that has a rotating connection to the retract screw 9. The flange capture nut 20 keys to the syringe carrier 19 and also keys to the middle housing 6.

A delay nut 17 with left-handed threads 35 that engage the center screw 10. The delay nut 17 sits on the end of the middle screw 16 and drives the center screw 10 after the middle screw 16 releases until the center screw 10 bottoms out the plunger 7.

Damping grease 33, along with a rotational detent 32, connects the delay nut 17 and the middle screw 16.

A syringe carrier 19 that supports the syringe flange 18, keys to the flange capture nut 20, keys to the center screw 10, and clips onto the center screw 10 proximal to the syringe flange 18.

An upper housing 11 that snaps 26 to the middle housing 6. The upper housing 11 has keyways to retain the lock ring 13. The upper housing 11 is coupled with the power spring 12 through the power spring's 12 outer tab and has slots 28 to allow the button 14 to rotate and press.

A middle housing 6 with left-handed threads 27 that engage the retract screw 9. The middle housing 6 keys to the flange capture nut 20, and snaps 26 to the upper housing 11 and snaps 25 to the lower housing 5.

A lower housing 5 which snaps 25 to the middle housing 6 and has a cam surface for the basecap 1.

A basecap 1 that has a cam surface to the lower housing 5. The basecap 1 protects the activation sleeve 22 and retains the RNS puller 23.

A rigid needle shield 2 that, when placed on the syringe 4, protects the syringe needle 3.

An RNS (rigid needle shield) puller 23 that snaps to the basecap 1.

An activation sleeve 22 that slides inside the lower housing 5. The activation sleeve 22 has a light spring 21 that keeps it in an extended position until use. The activation sleeve 22 can also be used as an interlock.

A button 14 that can rotate and press within the upper housing 11. Rotating the button 14 unlocks the device. Pressing the button 14 pushes the lock ring 13 distally to activate the device.

A lock ring 13 that keys to the upper housing 11. The lock ring 13 has splines 39 that retain the drive nut 15 and the power spring 12 in storage. It also has slots 29 that allow rotation of the button 14 and allow the button 14 to slide the lock ring 13 distally.

Action

To activate the device, the button 14 is rotated until the button 14 can be pressed. Upon pressing the button 14, the lock ring 13 slides off the drive nut 15, which allows the power spring 12 to transfer energy to the drive nut 15. The drive nut 15 rotates, but does not translate. The drive nut 15 is keyed to the middle screw 16. The rotation of the drive nut 15 spins the middle screw 16 through a spline coupling. The external threads of the middle screw 36 engage the internal threads 30 of the retract screw 9. When the drive nut 15 spins the middle screw 16, the middle screw 16 spins and extends, guided by the internal threads of the retract screw 30. The retract screw 9 is stationary during insertion and injection.

The double-acting screw mechanism effects insertion and fluid injection. The middle screw 16 has internal threads 37 that engage the threads of the center screw 10. When the middle screw 16, driven by the drive nut 15, spins, the center screw 10 begins to translate in the distal direction. The center screw 10 has a larger pitch than the external threads of the middle screw 36, which causes the center screw 10 to translate at a faster rate than the middle screw 16. The action of the center screw 10 pushes the syringe 4 until the syringe is fully extended; this is the insertion stage. Once the syringe has reached full extension, the continued action of the center screw 10 pushes the plunger 7, causing the fluid contents in the syringe 4 to empty out of the syringe 4; this begins the injection stage. The delay nut 17 follows along by the resistance due to the damping grease 33 and the light rotational detent 32 between the delay nut 17 and the middle screw 16. When the middle screw 16 falls off the threads at the end of the center screw 10, it no longer drives the center screw 10 directly. Instead, the delay nut 17, which is coupled with the middle screw 16 through the damping grease 33 and rotational detent 32, continues to advance the center screw 10. At the end of stroke, the center screw 10 bottoms the plunger 7, preventing the center screw 10 from advancing further.

At the end of stroke, when the center screw 10 is no longer advancing, the drive nut 15 ceases rotation. The torque from the power spring 12 provides enough energy for the middle screw 16 to overcome the rotational detent 32 between the delay nut 17 and the middle screw 16. The middle screw 16 will continue rotating, shearing the damping grease 33 which slows the rotation of the middle screw 16. This action provides the delay between completion of injection and the mechanism of retraction.

After injection, when the middle screw 16 reaches the end of travel in the retract screw 9, the middle screw 16 no longer backs up the latches 24 that keeps the retract screw 9 from rotating in the middle housing 6. When the middle screw 16 reaches the end of the thread stop in the retract screw 9, cutouts in the proximal end of the middle screw 34 allow the retract screw latches 24 to release. The release of the retract screw latches 24 from the middle housing 6 transfers the torque from the power spring 12 to the retract screw 9, allowing the retract screw 9 to retract the entire mechanism, including the syringe 4. The threads on the outer diameter of the retract screw 31 engage the inner diameter threads of the middle housing 27. The threads of the retract screw's outer diameter 31 are opposite in direction from the threads of its inner diameter 30. These opposing threads allow the retract screw 9 to rotate in the same direction as the middle screw 16, but to translate in the opposite direction. The rotation of the retract screw 9 causes it to translate in the proximal direction. Since the retract screw 9 is coupled to the syringe 4 through the flange capture nut 20, the entire mechanism with the syringe 4 will retract with the retract screw 9. The gap between the delay nut 17 and the syringe carrier 19 allows the delay nut 17 to fall off the end of the threads of the center screw 10, which rotationally decouples the mechanism from the center screw 10. The flange capture nut 20 maintains the axial connection between the rotational mechanism, the syringe 4, and the center screw 10. The decoupling allows the retract screw 9 to spin freely, quickly retracting the assembly. A slight gap between the flange capture nut 20 flange and the retract screw 9 flange may be required to allow the mechanism to release upon retract initiation. Lockout is automatic due to the thread stop between the middle housing 6 and the retract screw 31 when driven by the torque from the power spring 12.

Other Retract Mechanism Configuration

The center screw 10 is keyed to a tab disk 40, instead of the syringe carrier 19. There is no delay nut 17. The tab disk 40 is keyed to the retract screw 9. The tab disk 40 is composed of two similar disks, the upper tab disk 41 and the lower tab disk 42, that are coupled by a layer of damping grease. The upper tab disk 41 is keyed to the retract screw 9 and the center screw 10. The lower tab disk 42 is keyed only to the center screw. The center screw 10 does not have continuous thread; there is at least 1 keyway along its length. During most of the stroke, the upper tab disk 41 keeps the center screw 10 from rotating. At the end of stroke, the key of the upper tab disk 41 releases from the keyway in the center screw 10, allowing the center screw 10 to rotate. The damping grease that lightly couples the upper 41 and lower tab disks 42 together slows the rotation of the mechanism after the center screw 10 bottoms out the plunger 7. When the retract screw 9 is released, the center screw 10 rotates with the retract screw 9, thus eliminating any resistance. The mechanism retracts freely. A foot on a rotary bearing (not shown) allows the center screw 10 to release under load.

What is claimed:

1. An autoinjector having a central axis within a housing, comprising:

- a power spring disposed at a proximal end of the autoinjector;
- a drive nut connected at the distal end to the power spring;
- a middle screw cylindrically disposed about the drive nut, wherein the drive nut comprises keys that drive the middle screw;
- wherein the middle screw is an outer part of a double-acting screw and a center screw is an inner part of the double-acting screw;
- wherein threads of an inner diameter of the middle screw and outer diameter of the center screw interact so that rotation of the middle screw, when driven by the drive nut, causes the center screw to advance in the distal direction;
- a syringe disposed along the central axis and comprising a plunger and a tip or needle hub disposed distally of the center screw so that movement of the center screw pushes the plunger;

a retract screw cylindrically disposed about the middle screw and having threads on the outer circumference that match with threads on the inner circumference of the housing such that rotation of the middle screw, which comprises threads on its outer diameter that engage the retract screw, moves the retract screw in the proximal direction.

2. The autoinjector of claim 1, further comprising a delay nut disposed on the distal end of the middle screw and having damping grease disposed between the middle screw and the delay screw.

3. The autoinjector of claim 1, further comprising a power spring that is bi-metallic that causes changes in torsion that are temperature-dependent.

4. The autoinjector of claim 1, further comprising a middle screw whose outer diameter threads have a smaller pitch than the threads of a center screw, causing the center screw to advance in the distal direction at a faster rate than the middle screw.

5. The autoinjector of claim 1, further comprising a middle screw and a center screw that have threads in the same direction with varying pitch, providing the capability of effecting force multiplication or reduction.

6. The autoinjector of claim 1, further comprising a middle screw and a center screw that have threads in the opposite direction with varying pitch, providing the capability of effecting force multiplication or reduction.

7. The autoinjector of claim 1, further comprising a double-acting screw wherein the external threads of the middle screw and the threads of the center screw may vary in pitch along their respective lengths to vary the force applied during a stroke.

8. The autoinjector of claim 1, further comprising a flange capture nut that connects the syringe axially via a syringe carrier to the retract screw, allowing the syringe to retract with the retract screw.

9. An autoinjector having a central axis within a housing, comprising:

a temperature-compensated power spring comprising a torsion spring that is bi-metallic so that the torque provided by the power spring remains consistent over a range of temperatures;

a drive nut;

a double-acting screw, comprising a middle screw and a center screw;

a retract screw;

wherein the drive nut is connected at the distal end to the power spring and is keyed to the middle screw;

wherein the middle screw is disposed about the drive nut and the center screw;

wherein the middle screw is keyed to the center screw and retract screw; and wherein the retract screw is disposed about the middle screw.

10. The autoinjector of claim 9 further comprising:

a syringe disposed along the central axis and comprising a plunger and a tip or needle hub disposed distally of the center screw so that movement of the center screw pushes the plunger;

and further characterized by:

wherein the drive nut comprises keys that drive the middle screw;

wherein the middle screw is cylindrically disposed about the drive nut; and wherein threads of an inner diameter of the middle screw and outer diameter of the center screw interact so that rotation of the middle screw, when driven by the drive nut, causes the center screw to advance in the distal direction.

11. The autoinjector of claim 10, wherein the middle screw comprises outer diameter threads that have a smaller pitch than the threads of the center screw, causing the center screw to advance in the distal direction at a faster rate than the middle screw.

12. The autoinjector of claim 10, wherein the middle screw and the center screw have threads in the same direction with varying pitch, providing the capability of effecting force multiplication or reduction.

13. The autoinjector of claim 10, wherein the middle screw and the center screw have threads in the opposite direction with varying pitch, providing the capability of effecting force multiplication or reduction.

14. The autoinjector of claim 9, further comprising the retract screw cylindrically disposed about the middle screw and having threads on the outer circumference that match with threads on the inner circumference of the housing such that rotation of the middle screw, which comprises threads on its outer diameter that engage the retract screw, moves the retract screw in the proximal direction.

15. The autoinjector of claim 9, further comprising a delay nut disposed on the distal end of the middle screw and having damping grease disposed between the middle screw and the delay nut.

16. The autoinjector of claim 9, further comprising a flange capture nut that connects a syringe axially via a syringe carrier to the retract screw, allowing the syringe to retract with the retract screw.

17. The autoinjector of claim 9, wherein the center screw is prevented from rotating by being keyed to a syringe carrier that is keyed to a flange capture nut that is keyed to the housing or is keyed to a tab disk that is keyed to the retract screw.

18. The autoinjector of claim 9, further comprising a delay mechanism comprising a delay nut, the middle screw, and damping grease between the delay nut and the middle screw, wherein the delay nut stops rotating and the middle screw rotates at a slower rate due to the damping grease.

19. The autoinjector of claim 9, further comprising a retract mechanism comprising the retract screw circumferentially disposed around the middle screw, wherein the retract screw is locked until the middle screw releases the retract screw, allowing the retract screw to move in the proximal direction.

20. The autoinjector of claim 9, further comprising a retract mechanism comprising the retract screw and a tab disk, wherein the tab disk comprises an upper tab disk keyed to the retract screw, a lower tab disk keyed to the center screw, and damping grease disposed between the upper tab disk and lower tab disk.

* * * * *